United States Patent [19]

Schuetz et al.

[11] Patent Number: 5,157,037
[45] Date of Patent: Oct. 20, 1992

[54] α-ARYLACRYLATES SUBSTITUTED BY A HETEROCYCLIC RADICAL, AND FUNGICIDES WHICH CONTAIN THESE COMPOUNDS

[75] Inventors: Franz Schuetz, Ludwigshafen; Thomas Kuekenhoehner, Frankenthal; Jochen Wild, Deidesheim; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 376,999

[22] Filed: Jul. 7, 1989

[30] Foreign Application Priority Data

Jul. 15, 1988 [DE] Fed. Rep. of Germany ....... 3823991

[51] Int. Cl.$^5$ .................. A61K 31/505; C07D 239/02; C07D 213/79
[52] U.S. Cl. ..................... 514/269; 514/274; 514/311; 514/312; 514/348; 514/350; 544/298; 544/318; 544/319; 546/153; 546/156; 546/261; 546/263
[58] Field of Search ............... 546/263, 261, 134, 156; 544/298, 318, 319; 514/345, 350, 312, 311, 274, 269, 248

[56] References Cited

U.S. PATENT DOCUMENTS

| 4,120,692 | 10/1978 | Plant et al. | 71/94 |
|---|---|---|---|
| 4,675,328 | 6/1987 | Cassal et al. | 514/345 |
| 4,680,299 | 7/1987 | Hesson | 514/311 |
| 4,709,078 | 11/1987 | Schirmer et al. | 560/60 |
| 4,723,034 | 2/1988 | Schirmer et al. | 560/60 |
| 4,782,177 | 11/1988 | Schirmer et al. | 560/60 |
| 4,822,806 | 4/1989 | Ackermann | 514/345 |
| 4,822,908 | 4/1989 | Karbach et al. | 560/60 |
| 4,952,720 | 8/1990 | Schuetz et al. | 560/106 |
| 5,021,581 | 6/1991 | Clough | 546/309 |

FOREIGN PATENT DOCUMENTS

| 178826 | 4/1986 | European Pat. Off. |  |
|---|---|---|---|
| 0244077 | 3/1987 | European Pat. Off. |  |
| 242070 | 10/1987 | European Pat. Off. |  |
| 242081 | 10/1987 | European Pat. Off. |  |
| 278595 | 8/1988 | European Pat. Off. |  |
| 2999694 | 1/1989 | European Pat. Off. |  |
| 9050136 | 9/1972 | Japan | 514/312 |
| 2117760 | 6/1983 | United Kingdom | 514/345 |
| 2172595 | 9/1986 | United Kingdom . |  |

Primary Examiner—Jane T. Fan
Assistant Examiner—Celia Chang
Attorney, Agent, or Firm—Oblon, Spivak, McClelland, Maier & Neustadt

[57] ABSTRACT

α-Arylacrylates substituted by a heterocyclic radical and of the general formula I

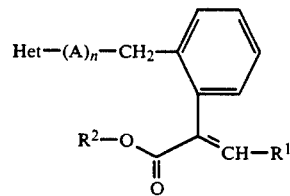

where $R^1$ is alkoxy or alkylthio, $R^2$ is alkyl, Het is pyridyl, pyridone, quinolyl, pyrimidinyl, pyrimidinone, the heterocyclic ring system being unsubstituted or substituted, A is carbonyloxy, oxygen or sulfur, and n is 0 or 1, and their plant-tolerated acid addition salts and metal complexes, and the N-oxides of the heterocyclic compounds, and fungicides containing these compounds.

8 Claims, No Drawings

α-ARYLACRYLATES SUBSTITUTED BY A HETEROCYCLIC RADICAL, AND FUNGICIDES WHICH CONTAIN THESE COMPOUNDS

The present invention relates to useful novel α-arylacrylates substituted by a heterocyclic radical and having a fungicidal action, and fungicides which contain these compounds.

It is known that methyl acrylates, for example methyl α-(2-benzyloxyphenyl)-β-methoxyacrylate or methyl α-(2-pyrid-2-yloxyphenyl)-β-methoxyacrylate or methyl α-(2-(6-methylpyrid-2-yl)-oxyphenyl)-β-methoxyacrylate or methyl α-(2-phenoxymethylphenyl)-β-methoxyacrylate (EP-178 826, 242 070 and 242 081) can be used as fungicides. However, their fungicidal action is unsatisfactory.

We have found that α-arylacrylates which are substituted by a heterocyclic radical and are of the general formula I

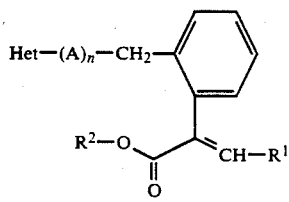

where $R^1$ is $C_1$-$C_4$-alkoxy or $C_1$-$C_4$-alkylthio, $R^2$ is $C_1$-$C_4$-alkyl, Het is pyridyl, pyrid-2-on-1-yl, pyrid-4-on-1-yl, quinolyl, pyrimidinyl, pyrimidin-2-on-1-yl, pyrimidin-4-on-1-yl or pyrimidin-6-on-1-yl, the heterocyclic ring system being unsubstituted or substituted by halogen, $C_1$-$C_8$-alkyl, $C_3$-$C_6$-cycloalkyl, $C_1$- or $C_2$-haloalkyl, $C_1$-$C_4$-alkoxy, $C_1$-$C_4$-alkylthio, $C_1$-$C_4$-alkoxy-$C_1$-$C_4$-alkyl, aryl, aryl-$C_1$-$C_4$-alkyl, $C_1$-$C_4$-alkylcarbonyl, $C_1$-$C_4$-alkoxycarbonyl or cyano, A is carbonyloxy, oxygen or sulfur and n is 0 or 1, and their plant-tolerated acid addition salts and metal complexes and the N-oxides of the heterocyclic compounds have an excellent fungicidal action, which is better than that of the known methyl acrylates.

The radicals mentioned in the general formula may have, for example, the following meanings: $R^1$ may be, for example, $C_1$-$C_4$-alkoxy (for example methoxy, ethoxy, n-propoxy, isopropoxy or butoxy) or $C_1$-$C_4$-alkylthio (for example methylthio, ethylthio, n-propylthio, isopropylthio or butylthio).

$R^2$ may be, for example, $C_1$-$C_4$-alkyl (for example methyl, ethyl, n-propyl, isopropyl, n-butyl, isobutyl, sec-butyl or tert-butyl).

Het may be, for example, pyrid-2-yl, pyrid-3-yl, pyrid-4-yl, pyrid-2-on-1-yl, pyrid-4-on-1-yl, quinol-2-yl, quinol-3-yl, quinol-4-yl, quinol-8-yl, pyrimidin-2-yl, pyrimidin-4-yl, pyrimidin-5-yl, pyrimidin-2-on-1-yl, pyrimidin-4-on-1-yl or pyrimidin-6-on-1-yl, and the heterocyclic ring system may be unsubstituted or substituted by one to three of the following radicals: halogen (for example fluorine, chlorine or bromine), $C_1$-$C_8$-alkyl (for example methyl, ethyl, n-propyl, isopropyl, n-butyl, isobutyl, sec-butyl, tert-butyl, n-pentyl, isopentyl, sec-pentyl, tert-pentyl, or neopentyl, hexyl, heptyl or octyl), $C_3$-$C_6$-cycloalkyl (for example cyclopropyl, cyclobutyl, cyclopentyl or cyclohexyl), $C_1$- or $C_2$-haloalkyl (for example difluoromethyl, trifluoromethyl, chloromethyl, dichloromethyl, trichloromethyl or pentafluoroethyl), $C_1$-$C_4$-alkoxy (for example methoxy, ethoxy, n-propoxy, or isopropoxy, n-butoxy, isobutoxy, sec-butoxy or tert-butoxy), $C_1$-$C_4$-alkoxy-$C_1$-$C_4$-alkyl (for example methoxymethyl, ethoxymethyl, methoxyethyl or propoxymethyl), aryl (for example phenyl), aryl-$C_1$-$C_4$-alkyl (for example benzyl, 2-phenylethyl, 3-phenylpropyl or 4-phenybutyl), $C_1$-$C_4$-alkylcarbonyl (for example acetyl, ethylcarbonyl, propylcarbonyl or butylcarbonyl), $C_1$-$C_4$-alkoxycarbonyl (for example methoxycarbonyl, ethoxycarbonyl, propoxycarbonyl or butoxycarbonyl), cyano, $C_1$-$C_4$-alkylthio (for example methylthio, ethylthio, propylthio).

The radical A mentioned in the general formula I may be, for example, carbonyloxy, oxygen or sulfur.

Where n is 0, $(A)_n$ is a single bond.

The compounds where n is 1 are preferred. When n is 0, the heterocyclic CO-containing radicals are bonded in the 1-position, i.e. via N, to the $CH_2$ group of the phenyl radical.

The novel compounds can also be converted by reaction with acids into plant-tolerated acid addition salts of the inorganic or organic acids, for example into salts of hydrochloric acid, hydrobromic acid, nitric acid, oxalic acid, acetic acid, sulfuric acid, phosphoric acid or dodecylbenzenesulfonic acid. The activity of the salts is due to the cation, so that in general any anion may be chosen.

Furthermore, the novel compounds can be converted into metal complexes by known methods. This can be carried out by reacting these compounds with the metal salts, for example salts of the metals copper, zinc, iron, manganese or nickel, e.g. copper(II) chloride, zinc(II) chloride, iron(III) chloride, copper(II) nitrate, manganese(II) chloride or nickel(II) bromide.

By reacting the novel compounds with oxidizing agents, for example with m-chloroperbenzoic acid, the N-oxides of the heterocyclic compounds are obtained.

The novel compounds can be prepared, for example, by the following processes:

The novel compounds of the general formula Ia (Het is pyridyl, quinolyl or pyrimidinyl, A is carbonyloxy, n is 1 and $R^1$ and $R^2$ each have the abovementioned meanings) are prepared, for example, by reacting an α-(2-bromomethylphenyl)-acrylate of the general formula III with an alkali metal salt, alkaline earth metal salt or ammonium salt of a heterocyclic carboxylic acid IV in a solvent or diluent and with or without the addition of a catalyst.

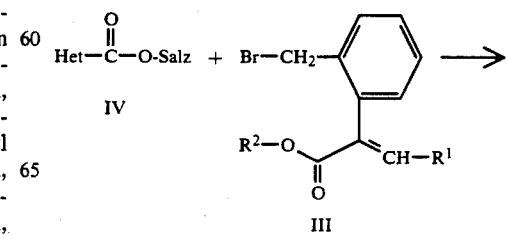

-continued

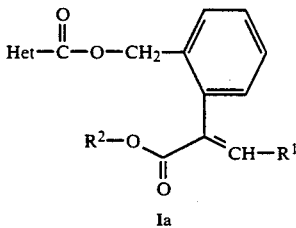

The preparation of carboxylic esters from alkyl halides and carboxylates is known per se (cf. for example Synthesis 1975, 805).

Examples of suitable solvents or diluents for the reaction of III with IV are acetone, acetonitrile, dimethyl sulfoxide, dioxane, dimethylformamide, N-methylpyrrolidone, N,N'-dimethylpropyleneurea and pyridine. It may also be advantageous to add a catalyst, for example tetramethylethylenediamine or tris-(3,6-dioxaheptyl)-amine, to the reaction mixture (cf. J. Org. Chem. 50 (1985), 3717).

The corresponding reactions can also be carried out in a two-phase system (e.g. carbon tetrachloride water). Examples of suitable phase-transfer catalysts are trioctylmethylammonium chloride and cetyltrimethylammonium chloride (cf. Synthesis 1974, 867, and J. Amer. Chem. Soc. 110 (1988), 185).

The heterocyclic carboxylates of the general formula IV can be prepared in a known manner from the corresponding carboxylic acids and bases (for example potassium hydroxide) in an inert solvent (for example ethanol).

α-Bromomethylphenylacrylates of the general formula III are disclosed in DE-35 19 280, DE-35 45 318 and DE-35 45 319.

For the preparation of the novel compounds of the general formula Ib (where Het is pyridyl, quinolyl or pyrimidinyl, A is oxygen or sulfur, n is 1 and $R^1$ and $R^2$ each have the abovementioned meanings), the heterocyclic compounds of the general formula Het—AH (II) are reacted with α-bromomethylphenylacrylates of the general formula III.

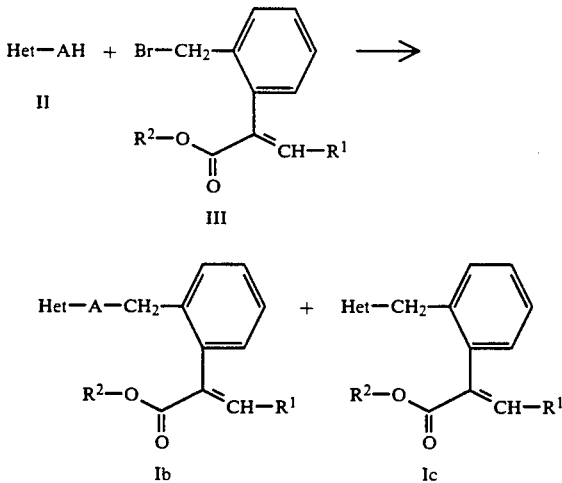

The novel compounds of the general formula Ic (where Het is pyrid-2-on-1-yl, pyrid-4-on-1-yl, pyrimidin-2-on-1-yl, pyrimidin-4-on-1-yl or pyrimidin-6-on-1-yl, n is 0 and $R^1$ and $R^2$ each have the abovementioned meanings) are formed in the reaction of the heterocyclic compounds of the general formula Het—OH IIa with α-bromomethylphenylacrylates of the general formula III in accordance with the above equation.

A compound Het—OH, for example 2-hydroxypyridine, can react in two tautomeric forms

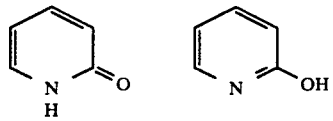

i.e. as 2-hydroxypyridine or pyrid-2-one.

Accordingly, the reaction with the bromomethyl compound takes place at N or at O, i.e. in the 1-position or in the 2-position. The same applies, for example, to the compound pyrid-4-one.

The end products which contain the CO group in the ring of the heterocyclic radical are bonded via N, i.e. in the 1-position, to the CH2 group of the benzyl radical.

The compounds of the general formula Ic are structural isomers of the corresponding compounds of the general formula Ib. The product distribution between Ib and Ic is dependent on the substituents on the heterocyclic structure. The percentage of Ic in the total yield (Ib+Ic) may be from 0 to 100%.

The structural isomers Ib and Ic can be separated into the pure compounds in a conventional manner, for example by fractional crystallization or by chromatography.

The reactions to give the compounds Ib and Ic can be carried out, for example in an inert solvent or diluent (for example acetone, acetonitrile, dimethyl sulfoxide, dioxane, dimethylformamide, N-methylpyrrolidone, N,N'-dimethylpropyleneurea or pyridine) using a base (for example sodium carbonate or potassium carbonate). It may also be advantageous to add a catalyst, for example tris-(3,6-dioxaheptyl)-amine, to the reaction mixture (J. Org. Chem. 50 (1985), 3717).

In an alternative procedure, it is also possible first to convert the compounds of the general formula II into the corresponding sodium or potassium salts with a base (for example sodium hydroxide or potassium hydroxide), and then to react these salts in an inert solvent or diluent (for example dimethylformamide) with the α-bromomethylphenylacrylates III to give the corresponding compounds of the general formula Ib or Ic.

The heterocyclic starting compounds of the general formula Het—$(A)_n$—H (where Het, n and A have the abovementioned meanings) are either known or can be prepared by processes similar to the known processes. Appropriate preparation processes are described in, for example, EP 224 217, DE-25 31 035, J. Heterocyclic Chem. 20 (1983), 219, and J. Heterocyclic Chem. 24 (1987), 709.

Because of their C=C double bond, the novel compounds of the general formula I can occur both as E isomers and as Z isomers. Both the individual isomeric compounds and their mixtures are embraced by the invention and can be used as fungicides. Preferably, the mixtures obtained in the synthesis are used as fungicides.

The Examples which follow illustrate the preparation of the novel active ingredients.

EXAMPLE 1

Methyl α-[2-(pyrid-3'-yl)-carbonyloxymethylphenyl]-β-methoxyacrylate (compound no. 13)

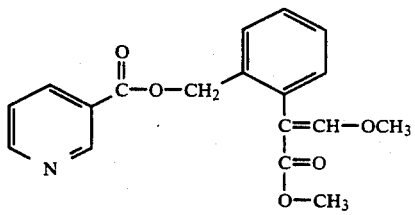

12.3 g (0.1 mole) of nicotinic acid and 5.6 g (0.1 mole) of potassium hydroxide are dissolved in 150 ml of ethanol and the solution is stirred for two hours at room temperature (20° C.). The white precipitate which separates out is filtered off under suction, washed with diethyl ether and suspended in 300 ml of dimethylformamide. Thereafter, 28.5 g (0.1 mole) of methyl α-(2-bromomethylphenyl)-β-methoxyacrylate are added. The reaction mixture is stirred for two hours at 110° C., left to cool and evaporated down, and the residue is taken up in methylene chloride. The organic phase is washed with water, dried over MgSO4 and evaporated down. The resulting oil is chromatographed over silica gel (5:1 cyclohexane/ethyl acetate). 23.9 g (73%) of the title compound are obtained as a colorless, viscous oil.

EXAMPLE 2

Methyl α-[2-(pyrid-2'-yl)-thiomethylphenyl]-α-methoxyacrylate (compound no. 53)

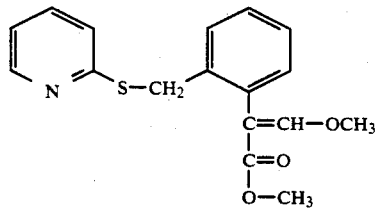

11.1 g (0.1 mole) of 2-mercaptopyridine, 28.5 g (0.1 mole) of methyl α-(2-bromomethylphenyl)-β-methoxyacrylate and 20.7 g (0.15 mole) of potassium carbonate in 250 ml of dimethylformamide are stirred for 48 hours at room temperature. Thereafter, the reaction mixture is evaporated down, the residue is taken up in methylene chloride and the organic phase is washed with water and dried over MgSO4. The oil obtained after evaporation is filtered over silica gel (cyclohexane). 14.5 g (46%) of the title compound are obtained as a colorless oil.

EXAMPLE 3

Methyl α-[2-(6'-methylpyrid-2'-yl)-oxymethylphenyl]-β-methoxyacrylate (compound no. 54) and methyl α-[2-(6'-methylpyrid-2'-on-1'-yl)-methylphenyl]-β-methoxyacrylate (compound no. 248)

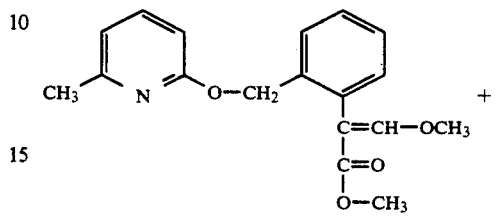 +

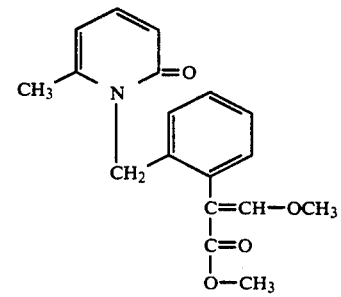

10.9 g (0.1 mole) of 6-methylpyrid-2-one, 28.5 g (0.1 mole) of methyl α-(2-bromomethylphenyl)-β-methoxyacrylate and 20.7 g (0.15 mole) of potassium carbonate in 250 ml of dimethylformamide are stirred for 48 hours at room temperature. Thereafter, the reaction mixture is evaporated down, the residue is taken up in methylene chloride and the organic phase is washed with water and dried over MgSO4. The oil obtained after evaporation is triturated with diethyl ether. 4.7 g (15%) of compound no. 248 are obtained in the form of colorless crystals. The mother liquor is evaporated down and the residue is triturated with diisopropyl ether. 10.6 g (34%) of compound no. 54 are now obtained in the form of colorless crystals.

EXAMPLE 4

Methyl α-[2-(4'-methylquinol-2'-yl)-oxymethylphenyl]-β-methoxyacrylate (compound no. 134)

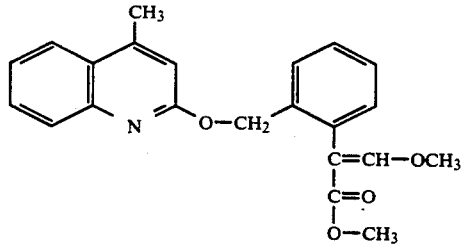

15.9 g (0.1 mole) of 4-methyl-2-hydroxyquinoline and 4.0 g (0.1 mole) of NaOH are dissolved in 150 ml of ethanol and the solution is stirred for 2 hours at room temperature. The precipitate which separates out is filtered off under suction, washed with diethyl ether and suspended in 400 ml of dimethylformamide. Thereafter, 28.5 g (0.1 mole) of methyl α-(2-bromomethylphenyl)-β-methoxyacrylate are added. The reaction mixture is stirred for 48 hours at room temperature and evaporated down, and the residue is taken up in methylene chloride. The organic phase is washed with water, dried over MgSO₄ and evaporated down. The resulting oil is chromatographed over silica gel (5:1 cyclohexane/ethyl acetate). 13.1 g (36%) of the title compound are obtained as a colorless oil.

EXAMPLE 5

Methyl α-[2-(pyrimid-4'-on-1'-yl)-methylphenyl]-β-methoxyacrylate (compound no. 252) and methyl α-[2-(pyrimid-6'-on-1'-yl)-methylphenyl]-β-methoxyacrylate (compound no. 253)

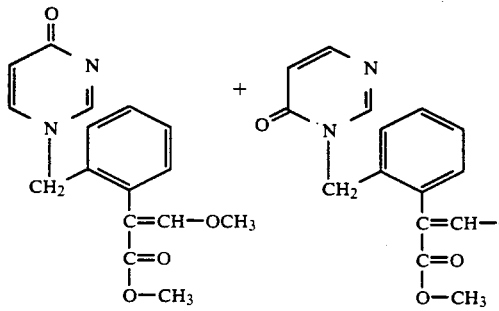

9.6 g (0.1 mole) of pyrimidin-4-one, 28.5 g (0.1 mole) of methyl α-(2-bromomethylphenyl)-β-methoxyacrylate and 20.7 g (0.15 mole) of potassium carbonate in 250 ml of dimethylformamide are stirred for 48 hours at room temperature. Thereafter, the precipitate is filtered off, the filtrate is evaporated down and the residue is taken up in methylene chloride. The organic phase is washed with water, dried over MgSO₄ and evaporated down. The resulting oil is chromatographed over silica gel (20:1 methylene chloride/methanol). 6.3 g (21%) of compound no. 253 are obtained in the form of colorless crystals by trituration with diisopropyl ether, and 6.3 g (21%) of compound no. 252 are obtained, likewise in the form of colorless crystals, by trituration with diethyl ether.

EXAMPLE 6

Methyl α-[2-(2',6'-bistrifluoromethylpyrimid-4'-yl)-oxy-methylphenyl]-β-methoxyacrylate (compound no. 202)

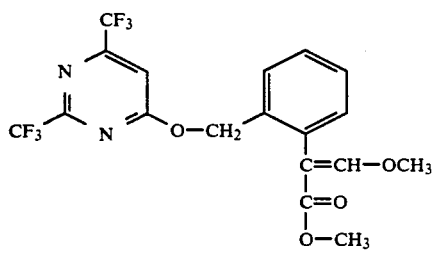

23.2 g (0.1 mole) of 2,6-bistrifluoromethyl-4-hydroxypyrimidine, 28.5 g (0.1 mole) of methyl α-(2-bromomethylphenyl)-β-methoxyacrylate and 20.7 g (0.15 mole) of potassium carbonate in 250 ml of dimethylformamide are stirred for 48 hours at room temperature. Thereafter, the reaction mixture is evaporated down, the residue is taken up in methylene chloride and the organic phase is washed with water and dried over MgSO₄. The oil obtained after evaporation is filtered over silica gel (cyclohexane). After the solvent has been removed, 24 g (55%) of the title compound is obtained in the form of colorless crystals.

The following compounds can be prepared in a similar manner:

TABLE 1

Compounds of the formula Ia (A = carbonyloxy, R¹ = OCH₃, R² = CH₃) The configuration statement refers to the β-methoxyacrylate group.

| No. | Het | mp. (isomer) |
|---|---|---|
| 1 | 2-pyridyl | oil (E) |
| 2 | 4-methyl-2-pyridyl | |
| 3 | 4-fluoro-2-pyridyl | |
| 4 | 4-chloro-2-pyridyl | |
| 5 | 6-methyl-2-pyridyl | |
| 6 | 6-ethyl-2-pyridyl | |
| 7 | 6-n-propyl-2-pyridyl | |
| 8 | 6-isopropyl-2-pyridyl | |
| 9 | 6-n-butyl-2-pyridyl | |
| 10 | 6-chloro-2-pyridyl | |
| 11 | 3,6-dichloro-2-pyridyl | |
| 12 | 5-n-butyl-2-pyridyl | |
| 13 | 3-pyridyl | oil (E) |
| 14 | 2-methyl-3-pyridyl | |
| 15 | 2-chloro-3-pyridyl | |
| 16 | 2-fluoro-3-pyridyl | |
| 17 | 4-chloro-3-pyridyl | |
| 18 | 5-fluoro-3-pyridyl | |
| 19 | 6-chloro-3-pyridyl | |
| 20 | 4-pyridyl | |
| 21. | 2-methyl-4-pyridyl | |
| 22 | 2,6-dimethyl-4-pyridyl | |
| 23 | 2,3-dimethyl-4-pyridyl | |
| 24 | 2-phenyl-3-methyl-4-pyridyl | |
| 25 | 3-methyl-4-pyridyl | |
| 26 | 2-ethyl-4-pyridyl | |
| 27 | 2-n-propyl-4-pyridyl | |
| 28 | 2-n-butyl-4-pyridyl | |
| 29 | 2-chloro-4-pyridyl | |
| 30 | 2,6-dichloro-4-pyridyl | |
| 31 | 2-quinolyl | |
| 32 | 3-quinolyl | 105–106° C. (E) |
| 33 | 4-quinolyl | |
| 34 | 2-methyl-4-quinolyl | |
| 35 | 2-ethyl-4-quinolyl | |
| 36 | 2-n-propyl-4-quinolyl | |
| 37 | 2-isopropyl-4-quinolyl | |
| 38 | 2-tert-butyl-4-quinolyl | |
| 39 | 2-cyclohexyl-4-quinolyl | |
| 40 | 3-methyl-4-quinolyl | |
| 41 | 3-ethyl-4-quinolyl | |
| 42 | 3-n-propyl-4-quinolyl | |
| 43 | 3-n-butyl-4-quinolyl | |
| 44 | 3-phenyl-4-quinolyl | |
| 45 | 3-benzyl-4-quinolyl | |
| 46 | 2-methyl-3-acetyl-4-quinolyl | |
| 47 | 2-phenyl-3-methoxy-4-quinolyl | |
| 48 | 2-methyl-3-cyano-4-quinolyl | |
| 49 | 6-methyl-4-quinolyl | |
| 50 | 6-chloro-4-quinolyl | |
| 51 | 7-chloro-4-quinolyl | |
| 52 | 7-chloro-8-methyl-3-quinolyl | |

TABLE 2

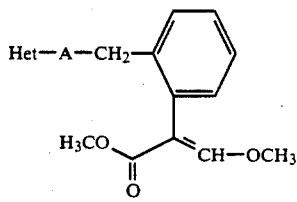

Compounds of the formula Ib ($R^1$ = $OCH_3$, $R^2$ = $CH_3$ n = 1) The configuration statement refers to the β-methoxyacrylate group.

| No. | Het | A | mp. (°C.) (isomer) |
|---|---|---|---|
| 53 | 2-pyridyl | S | oil (E) |
| 54 | 6-methyl-2-pyridyl | O | 79–80° C. (E) |
| 55 | 6-methyl-2-pyridyl | S | oil (E) |
| 56 | 6-ethyl-2-pyridyl | O | |
| 57 | 6-ethyl-2-pyridyl | S | |
| 58 | 6-n-propyl-2-pyridyl | O | |
| 59 | 6-n-propyl-2-pyridyl | S | |
| 60 | 6-isopropyl-2-pyridyl | O | |
| 61 | 6-isopropyl-2-pyridyl | S | |
| 62 | 6-n-butyl-2-pyridyl | O | |
| 63 | 6-n-butyl-2-pyridyl | S | |
| 64 | 6-tert.-butyl-2-pyridyl | O | |
| 65 | 6-tert.-butyl-2-pyridyl | S | |
| 66 | 6-n-pentyl-2-pyridyl | O | |
| 67 | 6-n-pentyl-2-pyridyl | S | |
| 68 | 6-n-hexyl-2-pyridyl | O | |
| 69 | 6-n-hexyl-2-pyridyl | S | |
| 70 | 6-phenyl-2-pyridyl | O | |
| 71 | 6-phenyl-2-pyridyl | S | |
| 72 | 6-benzyl-2-pyridyl | O | |
| 73 | 6-benzyl-2-pyridyl | S | |
| 74 | 6-trifluoromethyl-2-pyridyl | O | |
| 75 | 6-trifluoromethyl-2-pyridyl | S | |
| 76 | 6-methoxy-2-pyridyl | O | |
| 77 | 6-methoxy-2-pyridyl | S | |
| 78 | 6-chloro-2-pyridyl | O | 88–89 (E) |
| 79 | 6-chloro-2-pyridyl | S | |
| 80 | 3,6-dimethyl-2-pyridyl | O | |
| 81 | 3,6-dimethyl-2-pyridyl | S | |
| 82 | 3,6-diethyl-2-pyridyl | O | |
| 83 | 3,6-diethyl-2-pyridyl | S | |
| 84 | 4,6-dimethyl-2-pyridyl | O | |
| 85 | 4,6-dimethyl-2-pyridyl | S | |
| 86 | 5,6-dimethyl-2-pyridyl | O | |
| 87 | 5,6-dimethyl-2-pyridyl | S | |
| 88 | 4-phenyl-6-methyl-2-pyridyl | O | |
| 89 | 4-phenyl-6-methyl-2-pyridyl | S | |
| 90 | 4,6-diphenyl-2-pyridyl | O | |
| 91 | 4,6-diphenyl-2-pyridyl | S | |
| 92 | 3,4-dichloro-6-methyl-2-pyridyl | O | |
| 93 | 3,4-dichloro-6-methyl-2-pyridyl | S | |
| 94 | 3,4,5-trichloro-6-phenyl-2-pyridyl | O | |
| 95 | 3,4,5-trichloro-6-phenyl-2-pyridyl | S | |
| 96 | 4-trifluoromethyl-6-methyl-2-pyridyl | O | |
| 97 | 4-trifluoromethyl-6-methyl-2-pyridyl | S | |
| 98 | 3-acetyl-4,6-dimethyl-2-pyridyl | O | |
| 99 | 3-acetyl-4,6-dimethyl-2-pyridyl | S | |
| 100 | 3-cyano-6-methyl-2-pyridyl | O | 135–137 (E) |
| 101 | 3-cyano-6-methyl-2-pyridyl | S | |
| 102 | 3-cyano-6-ethyl-2-pyridyl | O | 177–178 (E) |
| 103 | 3-cyano-6-ethyl-2-pyridyl | S | |
| 104 | 3-cyano-6-n-propyl-2-pyridyl | O | |
| 105 | 3-cyano-6-n-propyl-2-pyridyl | S | |
| 106 | 3-cyano-6-isopropyl-2-pyridyl | O | 97–98 (E) |
| 107 | 3-cyano-6-isopropyl-2-pyridyl | S | 117–118 (E) |
| 108 | 3-cyano-6-cyclopropyl-2-pyridyl | O | 118–119 (E) |
| 109 | 3-cyano-6-cyclopropyl-2-pyridyl | S | |
| 110 | 3-cyano-6-n-butyl-2-pyridyl | O | |
| 111 | 3-cyano-6-n-butyl-2-pyridyl | S | |
| 112 | 3-cyano-6-tert.-butyl-2-pyridyl | O | 124–125 (E) |
| 113 | 3-cyano-6-tert.-butyl-2-pyridyl | S | |
| 114 | 3-cyano-6-cyclohexyl-2-pyridyl | O | |
| 115 | 3-cyano-6-cyclohexyl-2-pyridyl | S | |
| 116 | 3-cyano-6-phenyl-2-pyridyl | O | |
| 117 | 3-cyano-6-phenyl-2-pyridyl | S | |
| 118 | 3-methyloxycarbonyl-6-isopropyl-2-pyridyl | O | |

TABLE 2-continued

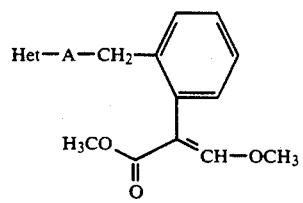

Compounds of the formula Ib ($R^1$ = $OCH_3$, $R^2$ = $CH_3$ n = 1) The configuration statement refers to the β-methoxyacrylate group.

| No. | Het | A | mp. (°C.) (isomer) |
|---|---|---|---|
| 119 | 3-methyloxycarbonyl-6-isopropyl-2-pyridyl | S | |
| 120 | 3-ethyloxycarbonyl-6-isopropyl-2-pyridyl | O | oil (E) |
| 121 | 3-ethyloxycarbonyl-6-isopropyl-2-pyridyl | S | |
| 122 | 3-cyano-4,6-dimethyl-2-pyridyl | O | 122–124 (E) |
| 123 | 3-cyano-4,6-dimethyl-2-pyridyl | S | |
| 124 | 3,5,6-trichloro-2-pyridyl | O | |
| 125 | 3,5,6-trichloro-2-pyridyl | S | |
| 126 | 5-trifluoromethyl-2-pyridyl | O | |
| 127 | 5-trifluoromethyl-2-pyridyl | S | 62–63 (E) |
| 128 | 3-chloro-5-trifluoromethyl-2-pyridyl | O | |
| 129 | 3-chloro-5-trifluoromethyl-2-pyridyl | S | oil (E) |
| 130 | 2-quinolyl | O | |
| 131 | 2-quinolyl | S | oil (E) |
| 132 | 3-methyl-2-quinolyl | O | |
| 133 | 3-methyl-2-quinolyl | S | |
| 134 | 4-methyl-2-quinolyl | O | oil (E) |
| 135 | 4-methyl-2-quinolyl | S | |
| 136 | 4-ethyl-2-quinolyl | O | |
| 137 | 4-ethyl-2-quinolyl | S | |
| 138 | 4-phenyl-2-quinolyl | O | |
| 139 | 4-phenyl-2-quinolyl | S | |
| 140 | 6-methyl-2-quinolyl | O | |
| 141 | 6-methyl-2-quinolyl | S | |
| 142 | 6-chloro-2-quinolyl | O | |
| 143 | 6-chloro-2-quinolyl | S | |
| 144 | 8-methyl-2-quinolyl | O | |
| 145 | 8-methyl-2-quinolyl | S | |
| 146 | 8-chloro-2-quinolyl | O | |
| 147 | 8-chloro-2-quinolyl | S | |
| 148 | 4-ethoxycarbonyl-2-quinolyl | O | |
| 149 | 4-ethoxycarbonyl-2-quinolyl | S | |
| 150 | 3,4-dimethyl-2-quinolyl | O | |
| 151 | 3,4-dimethyl-2-quinolyl | S | |
| 152 | 4-methyl-8-methoxy-2-quinolyl | O | |
| 153 | 4-methyl-8-methoxy-2-quinolyl | S | |
| 154 | 4-phenyl-8-ethoxy-2-quinolyl | O | |
| 155 | 4-phenyl-8-ethoxy-2-quinolyl | S | |
| 156 | 4-methyl-8-chloro-2-quinolyl | O | |
| 157 | 4-methyl-8-chloro-2-quinolyl | S | |
| 158 | 4-methyl-8-fluoro-2-quinolyl | O | |
| 159 | 4-methyl-8-fluoro-2-quinolyl | S | |
| 160 | 4-quinolyl | O | |
| 161 | 4-quinolyl | S | |
| 162 | 2-methyl-4-quinolyl | O | 129–130 (E) |
| 163 | 2-methyl-4-quinolyl | S | |
| 164 | 2-trichloromethyl-4-quinolyl | O | |
| 165 | 2-trichloromethyl-4-quinolyl | S | |
| 166 | 2-trifluoromethyl-4-quinolyl | O | |
| 167 | 2-trifluoromethyl-4-quinolyl | S | |
| 168 | 2-isopropyl-4-quinolyl | O | |
| 169 | 2-isopropyl-4-quinolyl | S | |
| 170 | 2-n-pentyl-4-quinolyl | O | |
| 171 | 2-n-pentyl-4-quinolyl | S | |
| 172 | 2-phenyl-4-quinolyl | O | |
| 173 | 2-phenyl-4-quinolyl | S | |
| 174 | 2-methoxycarbonyl-4-quinolyl | O | |
| 175 | 2-methoxycarbonyl-4-quinolyl | S | |
| 176 | 2,6-dimethyl-4-quinolyl | O | |
| 177 | 2,6-dimethyl-4-quinolyl | S | |
| 178 | 2-methyl-6-chloro-4-quinolyl | O | |
| 179 | 2-methyl-6-chloro-4-quinolyl | S | |
| 180 | 2-methyl-6-fluoro-4-quinolyl | O | |

TABLE 2-continued

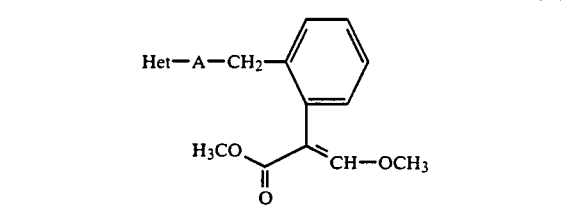

Compounds of the formula Ib ($R^1$ = $OCH_3$, $R^2$ = $CH_3$ n = 1) The configuration statement refers to the β-methoxyacrylate group.

| No. | Het | A | mp. (°C.) (isomer) |
|---|---|---|---|
| 181 | 2-methyl-6-fluoro-4-quinolyl | S | |
| 182 | 8-quinolyl | O | |
| 183 | 8-quinolyl | S | |
| 184 | 2-methyl-8-quinolyl | O | oil (E) |
| 185 | 2-methyl-8-quinolyl | S | |
| 186 | 5,7-dichloro-8-quinolyl | O | 106–107 (E) |
| 187 | 5,7-dichloro-8-quinolyl | S | |
| 188 | 4,6-dimethyl-2-pyrimidinyl | O | |
| 189 | 4,6-dimethyl-2-pyrimidinyl | S | 133–134 (E) |
| 190 | 4-trifluoromethyl-2-pyrimidinyl | O | |
| 191 | 4-trifluoromethyl-2-pyrimidinyl | S | 85–86 (E) |
| 192 | 4,5,6-trimethyl-2-pyrimidinyl | O | |
| 193 | 4,5,6-trimethyl-2-pyrimidinyl | S | |
| 194 | 4-benzyl-6-methyl-2-pyrimidinyl | O | |
| 195 | 4-benzyl-6-methyl-2-pyrimidinyl | S | |
| 196 | 4-methyl-6-phenyl-2-pyrimidinyl | O | |
| 197 | 4-methyl-6-phenyl-2-pyrimidinyl | S | |
| 198 | 4,6-dimethyl-5-chloro-2-pyrimidinyl | O | |
| 199 | 4,6-dimethyl-5-chloro-2-pyrimidinyl | S | |
| 200 | 2,6-dimethyl-4-pyrimidinyl | O | |
| 201 | 2,6-dimethyl-4-pyrimidinyl | S | |
| 202 | 2,6-bis-(trifluoromethyl)-4-pyrimidinyl | O | 57–58 (E) |
| 203 | 2,6-bis-(trifluoromethyl)-4-pyrimidinyl | S | |
| 204 | 2-chloromethyl-6-methyl-4-pyrimidinyl | O | |
| 205 | 2-chloromethyl-6-methyl-4-pyrimidinyl | S | |
| 206 | 2-methyl-6-chloromethyl-4-pyrimidinyl | O | |
| 207 | 2-methyl-6-chloromethyl-4-pyrimidinyl | S | |
| 208 | 2-isopropyl-6-methyl-4-pyrimidinyl | O | |
| 209 | 2-isopropyl-6-methyl-4-pyrimidinyl | S | |
| 210 | 2-isopropyl-6-chloromethyl-4-pyrimidinyl | O | |
| 211 | 2-isopropyl-6-chloromethyl-4-pyrimidinyl | S | |
| 212 | 2-cyclopropyl-6-chloromethyl-4-pyrimidinyl | O | |
| 213 | 2-cyclopropyl-6-chloromethyl-4-pyrimidinyl | S | |
| 214 | 2-cyclopropyl-6-methyl-4-pyrimidinyl | O | |
| 215 | 2-cyclopropyl-6-methyl-4-pyrimidinyl | S | |
| 216 | 2-methyl-6-methoxymethyl-4-pyrimidinyl | O | |
| 217 | 2-methyl-6-methoxymethyl-4-pyrimidinyl | S | |
| 218 | 2-isopropyl-6-methoxymethyl-4-pyrimidinyl | O | |
| 219 | 2-isopropyl-6-methoxymethyl-4-pyrimidinyl | S | |
| 220 | 2-phenyl-4-pyrimidinyl | O | |
| 221 | 2-phenyl-4-pyrimidinyl | S | |
| 222 | 2,5-dimethyl-4-pyrimidinyl | O | |
| 223 | 2,5-dimethyl-4-pyrimidinyl | S | |
| 224 | 2-methylthio-6-trifluoromethyl-4-pyrimidinyl | O | 111–112 (E) |
| 225 | 2-methylthio-6-trifluoromethyl-4-pyrimidinyl | S | |
| 226 | 2-methylthio-5-chloro-6-trifluoromethyl-4-pyrimidinyl | O | oil (E) |
| 227 | 2-methylthio-5-chloro-6-trifluoromethyl-4-pyrimidinyl | S | |
| 228 | 2-methylthio-5-n-octyl-6-methyl-4-pyrimidinyl | O | |
| 229 | 2-methylthio-5-n-octyl-6-methyl-4-pyrimidinyl | S | |
| 230 | 2-methyl-6-trifluoromethyl-4-pyrimidinyl | O | |
| 231 | 2-methyl-6-trifluoromethyl-4-pyrimidinyl | S | oil (E) |
| 232 | 2-n-propyl-6-trifluoromethyl-4-pyrimidinyl | O | 81–82 (E) |
| 233 | 2-n-propyl-6-trifluoromethyl-4-pyrimidinyl | S | |
| 234 | 2-isopropyl-6-trifluoromethyl-4-pyrimidinyl | O | |
| 235 | 2-isopropyl-6-trifluoromethyl-4-pyrimidinyl | S | |
| 236 | 2-tert.-butyl-6-trifluoromethyl-4-pyrimidinyl | O | |
| 237 | 2-tert.-butyl-6-trifluoromethyl-4-pyrimidinyl | S | |
| 238 | 2-methyl-5-chloro-6-trifluoromethyl-4-pyrimidinyl | O | |
| 239 | 2-methyl-5-chloro-6-trifluoromethyl-4-pyrimidinyl | S | |
| 240 | 2-n-propyl-5-chloro-6-trifluoromethyl-4-pyrimidinyl | O | |
| 241 | 2-n-propyl-5-chloro-6-trifluoromethyl-4-pyrimidinyl | S | |
| 242 | 2-isopropyl-5-chloro-6-trifluoromethyl-4-pyrimidinyl | O | |
| 243 | 2-isopropyl-5-chloro-6-trifluoromethyl-4-pyrimidinyl | S | |
| 244 | 2-tert.-butyl-5-chloro-6-trifluoromethyl-4-pyrimidinyl | O | |
| 245 | 2-tert.-butyl-5-chloro-6-trifluoromethyl-4-pyrimidinyl | S | |
| 246 | 2pPyrimidinyl | S | oil (E) |
| 255 | 3-ethyloxycarbonyl-6-cyclopropyl-2-pyridyl | O | oil (E) |
| 256 | 3-trifluoromethyl-6-isopropyl-2-pyridyl | O | oil (E) |
| 257 | 2-phenyl-6-trifluoromethyl-4-pyrimidinyl | O | 109–110 (E) |
| 258 | 2-methylthio-6-difluoromethyl-4-pyrimidinyl | O | 77–78 (E) |

TABLE 3

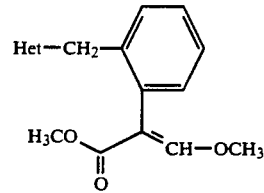

Compounds of the formula Ic (n = 0, $R^1$ = $OCH_3$, $R^2$ = $CH_3$) The configuration statement refers to the β-methoxyacrylate group.

| No. | Het | mp. (°C.) (isomer) |
|---|---|---|
| 247 | 2-pyridon-1-yl | 103–104 (E) |
| 248 | 6-methyl-2-pyridon-1-yl | 149–150 (E) |
| 249 | 3-cyano-6-methyl-2-pyridon-1-yl | 181–183 (E) |
| 250 | 4-pyridon-1-yl | 144–145 (E) |
| 251 | 2-pyrimidinon-1-yl | oil (E) |
| 252 | 4-pyrimidinon-1-yl | 85–86 (E) |
| 253 | 6-pyrimidinon-1-yl | 95–96 (E) |
| 254 | 2-n-propyl-4-trifluoromethyl-6-pyrimidinon-1-yl | 90–92 (E) |

TABLE 3-continued

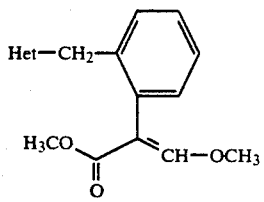

Compounds of the formula Ic (n = 0, $R^1$ = OCH$_3$, $R^2$ = CH$_3$) The configuration statement refers to the β-methoxyacrylate group.

| No. | Het | mp. (°C.) (isomer) |
|---|---|---|
| 259 | 4-trifluoromethyl-2-pyrimidon-1-yl | 219–220 (E) |
| 260 | 5-trifluoromethyl-2-pyridon-1-yl | oil (E) |
| 261 | 3-chloro-5-trifluoromethyl-2-pyridon-1-yl | 113–114 (E) |

TABLE 4

NMR data for selected compounds from Tables 1, 2 and 3. The chemical shift (δ) is stated in ppm relative to tetramethylsilane. The solvent was CDCl$_3$.

Compound no. 1
3.61 (s, 3H); 3.79 (s, 3H); 5.36 (s, 2H); 7.16–7.56 (m, 5H); 7.60 (s, 1H); 7.80 (t, 1H); 8.08 (d, 1H); 8.68 (d, 1H).

Compound no. 13
3.63 (s, 3H); 3.78 (s, 3H); 5.32 (s, 2H); 7.17–7.55 (m, 5H); 7.60 (s, 1H); 8.28 (d, 1H); 8.76 (d, 1H); 9.21 (s, 1H).

Compound no. 32
3.64 (s, 3H); 3.80 (s, 3H); 5.37 (s, 2H); 7.21–7.65 (m, 5H); 7.61 (s, 1H); 7.84 (t, 1H); 7.95 (d, 1H); 8.17 (d, 1H); 8.85 (s, 1H); 9.45 (s, 1H).

Compound no. 53
3.67 (s, 3H); 3.75 (s, 3H); 4.35 (s, 2H); 6.90–7.53 (m, 7H); 7.56 (s, 1H); 8.40 (d, 1H).

Compound no. 54
2.43 (s, 3H); 3.68 (s, 3H); 3.77 (s, 3H); 5.27 (s, 2H); 6.50 (d, 1H); 6.68 (d, 1H); 7.15–7.55 (m, 5H); 7.60 (s, 1H).

Compound no. 78
3.70 (s, 3H); 3.82 (s, 3H); 5.28 (s, 2H); 6.62 (d, 1H); 6.88 (d, 1H); 7.15–7.55 (m, 5H); 7.58 (s, 1H).

Compound no. 100
2.50 (s, 3H); 3.73 (s, 3H); 3.85 (s, 3H); 5.42 (s, 2H); 6.80 (d, 1H); 7.18–7.69 (m, 4H); 7.65 (s, 1H); 7.74 (d, 1H).

Compound no. 102
1.28 (t, 3H); 2.75 (q, 2H); 3.72 (s, 3H); 3.84 (s, 3H); 5.43 (s, 2H); 6.78 (d, 1H); 7.16–7.64 (m, 4H); 7.60 (s, 1H); 7.73 (d, 1H).

Compound no. 106
1.26 (d, 6H); 2.98 (quin., 1H); 3.72 (s, 3H); 3.84 (s, 3H); 5.44 (s, 2H); 6.79 (d, 1H); 7.18–7.67 (m, 4H); 7.63 (s, 1H); 7.74 (d, 1H).

Compound no. 108
1.05 (m, 4H); 1.96 (m, 1H); 3.72 (s, 3H); 3.85 (s, 3H); 5.35 (s, 2H); 6.83 (d, 1H); 7.16–7.55 (m, 4H); 7.63 (s, 1H); 7.65 (d, 1H).

Compound no. 122
2.42 (s, 3H); 2.43 (s, 3H); 3.71 (s, 3H); 3.86 (s, 3H); 5.38 (s, 2H); 6.67 (s, 1H); 7.14–7.63 (m, 4H); 7.61 (s, 1H).

Compound no. 131
3.68 (s, 3H); 3.75 (s, 3H); 4.60 (s, 2H); 7.08–7.65 (m, 8H); 7.53 (s, 1H); 7.77 (d, 1H); 7.93 (d, 1H).

Compound no. 134
2.60 (s, 3H); 3.68 (s, 3H); 3.79 (s, 3H); 5.43 (s, 2H); 6.75 (s, 1H); 7.13–7.87 (m, 8H); 7.57 (m, 1H).

Compound no. 162
2.65 (s, 3H); 3.69 (s, 3H); 3.80 (s, 3H); 5.16 (s, 2H); 6.57 (s, 1H); 7.20–7.67 (m, 6H); 7.57 (s, 1H); 7.93 (s, 1H); 8.19 (s, 1H).

Compound no. 184
2.80 (s, 3H); 3.72 (s, 3H); 3.79 (s, 3H); 5.39 (s, 2H); 6.85 (d, 1H); 7.16–7.28 (m, 6H); 7.64 (m, 2H); 7.95 (d, 1H).

Compound no. 186
3.68 (s, 3H); 3.79 (s, 3H); 5.42 (s, 2H); 7.16–7.60 (m, 4H); 7.50 (s, 1H); 7.65 (s, 1H); 8.04 (d, 1H); 8.53 (d, 1H); 9.02 (d, 1H).

Compound no. 202
3.68 (s, 3H); 3.83 (s, 3H); 5.50 (s, 2H); 7.16 (s, 1H); 7.20–7.58 (m, 4H); 7.60 (s, 1H).

Compound no. 224
2.55 (s, 3H); 3.69 (s, 3H); 3.81 (s, 3H); 5.40 (s, 2H); 6.68 (s, 1H); 7.29–7.54 (m, 4H); 7.60 (s, 1H).

Compound no. 226
2.57 (s, 3H); 3.72 (s, 3H); 3.84 (s, 3H); 5.48 (s, 2H); 7.20–7.60 (m, 4H); 7.62 (s, 1H).

Compound no. 232
1.01 (t, 3H); 1.87 (sext., 2H); 2.90 (t, 2H); 3.70 (s, 3H); 3.81 (s, 3H); 5.40 (s, 2H); 6.86 (s, 1H); 7.20–7.58 (m, 4H); 7.60 (s, 1H).

Compound no. 246
3.70 (s, 3H); 3.83 (s, 3H); 4.34 (s, 2H); 6.98 (t, 1H); 7.12–7.58 (m, 4H); 7.60 (s, 1H); 8.52 (d, 2H).

Compound no. 247
3.64 (s, 3H); 3.84 (s, 3H); 5.08 (s, broad, 2H); 6.05 (t, 1H); 6.56 (d, 1H); 7.07–7.35 (m, 6H); 7.57 (s, 1H).

Compound no. 249
2.20 (s, 3H); 3.71 (s, 3H); 3.88 (s, 3H); 5.26 (s, broad, 2H); 6.11 (d, 1H); 6.81 (d, 1H); 7.15–7.70 (m, 4H); 7.65 (s, 1H).

Compound no. 250
3.56 (s, 3H); 3.80 (s, 3H); 4.87 (s, 2H); 6.05 (d, 2H); 7.10–7.35 (m, 4H); 7.50 (d, 2H); 7.68 (s, 1H).

Compound no. 251
3.67 (s, 3H); 3.85 (s, 3H); 5.03 (s, 2H); 6.22 (m, 1H); 7.21–7.50 (m, 5H); 7.60 (s, 1H); 8.65 (m, 1H).

Compound no. 252
3.53 (s, 3H); 3.79 (s, 3H); 4.87 (s, 2H); 5.96 (d, 1H); 7.09–7.48 (m, 5H); 7.68 (s, 1H); 8.27 (d, 1H).

Compound no. 253
3.64 (s, 3H); 3.80 (s, 3H); 5.03 (s, broad, 2H); 6.44 (d, 1H); 7.17–7.39 (m, 4H); 7.59 (s, 1H); 7.84 (d, 1H); 7.92 (s, 1H).

Compound no. 254
0.88 (t, 3H); 1.68 (sext., 2H); 2.49 (t, 2H); 3.72 (s, 3H); 3.91 (s, 3H); 5.22 (s, broad, 2H); 6.80 (s, 1H); 6.87–7.33 (m, 4H); 7.68 (s, 1H).

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 53 is mixed with 10 parts by weight of N-methyl-α-pyrrolidone. A mixture is obtained which is suitable for application in the form of very fine drops.

II. 20 parts by weight of compound no. 131 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 162 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 246 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 53 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 131 is intimately mixed with 97 parts by weight of particulate kaolin. A dust is obtained containing 3% by weight of the active ingredient.

VII. 30 parts by weight of compound no. 162 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 246 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 53 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-2-(dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazole-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

The following prior art compounds were used for comparison purposes: methyl α-(2-benzyloxyphenyl)-β-methoxyacrylate (A) disclosed in DE 3,519,282; methyl α-(2-phenoxymethylphenyl)-β-methoxyacrylate (B) disclosed in DE 3,545,319; methyl α-2-(2-pyridyl)-oxyphenyl-β-methoxyacrylate (D) disclosed in EP 178,826; and methyl α-2-(6-methylpyridyl)oxyphenyl-β-methoxyacrylate (C) disclosed in EP 242,081.

USE EXAMPLE 1

Action on *Pseudocercosporella herpotrichoides*

Wheat plants of the "Frühgold" variety were sprayed to runoff at the one-leaf stage with aqueous formulations containing (dry basis) 80% (wt %) of active ingredient and 20% of emulsifier. After 24 hours the plants were inoculated with a spore suspension of *Pseudocercosporella herpotrichoides*. For optimum development of the plant disease the plants were then set up for one week in a climatic cabinet at from 16° to 18° C. and a relative humidity in excess of 95%. The plants were then cultivated for a further two weeks in the greenhouse at 15° to 17° C. The spread of the disease was then assessed on the lower portion of the plant stem.

The results show that compounds nos. 53, 100, 131, 162, 189 and 246, applied as 0.1% spray liquors, had a better fungicidal action (90%) than prior art active ingredients A and B (70%).

USE EXAMPLE 2

Action on wheat brown rust

Leaves of pot-grown wheat seedlings of the "Kanzler" variety were dusted with spores of brown rust (*Puccinia recondita*). The pots were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that compounds nos. 54, 78, 127, 129 and 256, applied as 0.0015% spray liquors, had a better fungicidal action (97%) than prior art compounds A, B, C and D (35%).

USE EXAMPLE 3

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse.

Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that compounds nos. 78, 100, 129, 191, 232 and 256, applied as 0.006% spray liquors, had a better fungicidal action (100%) than prior art active ingredients C and D (70%).

We claim:

1. A compound selected from the group consisting of a compound of formula I

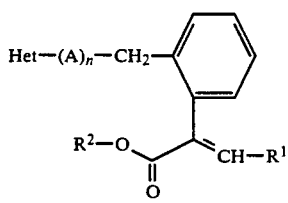

where $R^1$ is $C_1$–$C_4$-alkoxy or $C_1$–$C_4$-alkylthio, $R^2$ is $C_1$–$C_4$-alkyl, Het is pyridyl, pyrid-2-on-1-yl, pyrid-4-on-1-yl, quinolyl, pyrimidinyl, pyrimidin-2-on-1-yl, pyrimidin-4-on-1-yl or pyrimidin-6-on-1-yl, the heterocyclic ring system being unsubstituted or substituted by halogen, $C_1$–$C_8$-alkyl, $C_3$–$C_6$-cycloalkyl, $C_1$–$C_2$-haloalkyl, $C_1$–$C_4$-alkoxy, methylthio, $C_1$–$C_4$-alkoxy-$C_1$–$C_4$-alkyl, phenyl, phenyl-$C_1$–$C_4$-alkyl, $C_1$–$C_4$-alkylcarbonyl, $C_1$–$C_4$-alkoxycarbonyl or cyano, A is carbonyloxy, and n is 1, and its plant-tolerated acid addition salts and metal complexes, and N-oxides.

2. A method for combating fungi, comprising contacting the fungi, or the materials, plants, seed or soil to be protected against fungus attack with a fungicidally effective amount of a compound of the formula I

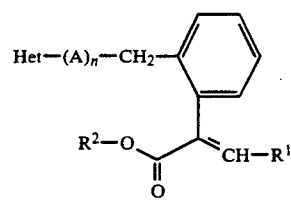

where $R^1$ is $C_1$–$C_4$-alkoxy or $C_1$–$C_4$-alkylthio, $R^2$ is $C_1$–$C_4$-alkyl, Het is pyridyl, pyrid-2-on-1-yl, pyrid-4-on-1-yl, quinolyl, pyrimidinyl, pyrimidin-2-on-1-yl, pyrimidin-4-on-1-yl or pyrimidin-6-on-1-yl, the heterocyclic ring system being unsubstituted or substituted by halogen, $C_1$–$C_8$-alkyl, $C_3$–$C_6$-cycloalkyl, $C_1$–$C_2$-haloalkyl, $C_1$–$C_4$-alkoxy, methylthio, $C_1$–$C_4$-alkoxy-$C_1$–$C_4$-alkyl, phenyl, phenyl-$C_1$–$C_4$-alkyl, $C_1$–$C_4$-alkylcarbonyl, $C_1$–$C_4$-alkoxycarbonyl or cyano, A is carbonyloxy, and n is 1, or a plant-tolerated acid addition salt or metal complex thereof, or an N-oxide thereof.

3. A fungicidal composition comprising an inert carrier and a fungicidally effective amount of a compound of the formula I

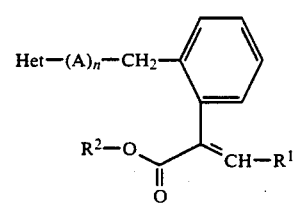

where $R^1$ is $C_1$–$C_4$-alkoxy or $C_1$–$C_4$-alkylthio, $R^2$ is $C_1$–$C_4$-alkyl, Het is pyridyl, pyrid-2-on-1-yl, pyrid-4-on-1-yl, quinolyl, pyrimidinyl, pyrimidin-2-on-1-yl, pyrimidin-4-on-1-yl or pyrimidin-6-on-1-yl, the heterocyclic ring system being unsubstituted or substituted by halogen, $C_1$–$C_8$-alkyl, $C_3$–$C_6$-cycloalkyl, $C_1$–$C_2$-haloalkyl, $C_1$–$C_4$-alkoxy, methylthio, $C_1$–$C_4$-alkoxy-$C_1$–$C_4$-alkyl, phenyl, phenyl-$C_1$–$C_4$-alkyl, $C_1$–$C_4$-alkylcarbonyl, $C_1$–$C_4$-alkoxycarbonyl or cyano, A is carbonyloxy, and n is 1, or a plant-tolerated acid addition salt or metal complex or N-oxide thereof.

4. A compound of claim 1, wherein Het is selected from the group consisting of 3-pyridyl, 2-pyridyl and 3-quinolyl, $R^1$ is methoxy, and $R^2$ is methyl.

5. A compound of the formula I

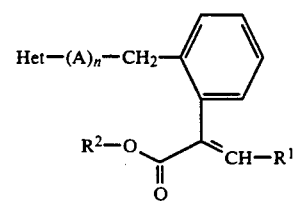

where $R^1$ is $C_1$–$C_4$-alkoxy or $C_1$–$C_4$-alkylthio, $R^2$ is $C_1$–$C_4$-alkyl, Het is pyrid-2-on-1-yl, pyrid-4-on-1-yl, pyrimidin-2-on-1-yl, pyrimidin-4-on-1-yl or pyrimidin- 6-on-1-yl, the heterocyclic ring system being unsubstituted or substituted by halogen, $C_1$–$C_8$-alkyl, $C_3$–$C_6$-cycloalkyl, $C_1$–$C_2$-haloalkyl, $C_1$–$C_4$-alkoxy, methylthio, $C_1$–$C_4$-alkoxy-$C_1$–$C_4$-alkyl, phenyl, phenyl-$C_1$–$C_4$-alkyl, $C_1$–$C_4$-alkylcarbonyl, $C_1$–$C_4$-alkoxycarbonyl or cyano, A is carbonyloxy, oxygen or sulfur, and n is 0 or 1, or a plant-tolerated acid addition salt, metal complex or N-oxide thereof.

6. A fungicidal composition comprising an inert carrier and a fungicidally effective amount of a compound of claim 5.

7. A method for combating fungi, comprising contacting the fungi, or the materials, plants, seed or soil to be protected against fungus attack with a fungicidally effective amount of a compound according to claim 5.

8. A compound of claim 5, wherein Het is selected from the group consisting of 2-pyridon-1-yl, 6-methyl-2-pyridon-1-yl, 3-cyano-6-methyl-2-pyridon-1-yl, 4-pyridon-1-yl, 2-pyrimidinon-1-yl, 4-pyrimidinon-1-yl, 6-pyrimidinon-1-yl, 2-n-propyl-4-trifluoromethyl-6-pyrimidinon-1-yl, 4-trifluoromethyl-2-pyrimidon-1-yl, 5-trifluoromethyl-2-pyridon-1-yl, and 3-chloro-5-trifluoromethyl-2-pyridon-1-yl, n is 0, $R^1$ is $OCH_3$, and $R^2$ is $CH_3$.

* * * * *